United States Patent [19]

Gedeon et al.

[11] Patent Number: 4,509,359
[45] Date of Patent: Apr. 9, 1985

[54] METHOD AND APPARATUS FOR MEASURING THE CONCENTRATION OF A GIVEN COMPONENT IN A GAS INHALED AND/OR EXHALED BY A PATIENT

[75] Inventors: Andras Gedeon, Täby; Lennart Mathiasson, Lund, both of Sweden

[73] Assignee: Gambro Engström AB, Bromma, Sweden

[21] Appl. No.: 448,802

[22] Filed: Dec. 10, 1982

[30] Foreign Application Priority Data

Dec. 23, 1981 [SE] Sweden .............................. 8107775

[51] Int. Cl.³ ............................................ G01N 31/00
[52] U.S. Cl. ........................................ 73/23; 73/1 G; 128/719
[58] Field of Search ................. 73/23, 19, 1 G, 29; 128/718, 719, 203.14, 203.16, 203.25; 55/158

[56] References Cited

U.S. PATENT DOCUMENTS

| | | | |
|---|---|---|---|
| 3,434,471 | 3/1969 | Liston | 128/203.14 |
| 3,735,559 | 5/1973 | Salemme | 55/158 |
| 3,895,630 | 7/1975 | Bachman | 73/23 |

FOREIGN PATENT DOCUMENTS 1028255  5/1973  Canada ................................ 55/158

OTHER PUBLICATIONS

D. E. Holness et al., "Temperature-Dependent Characteristics of Teflon Membranes Used in Mass Spec.", Med. Instr., vol. 8, No. 1, pp. 23-25, Jan.-Feb. 1975.

Primary Examiner—Stephen A. Kreitman
Attorney, Agent, or Firm—Browdy and Neimark

[57] ABSTRACT

For the purpose of measuring the concentration of one or more given components of the breathing gas of a patient there is removed a small part of the breathing gas at a location immediately in front of the mouth of the patient. The withdrawn gas is passed to a measuring instrument sensitive to the component or components of interest through a line which comprises, at least in part, a thin tube of a fluorosulfonyl polymer, and the outer surface of which is in free contact with the ambient air. In this way, the temperature and relative humidity of the breathing gas supplied to the measuring instrument are brought into agreement with the temperature and relative humidity of the ambient air. By calibrating the measuring instrument with respect to the temperature and relative humidity of the surrounding air prior to carrying out the measuring operation, the measuring procedure can be carried out without disturbances caused by variations in the relative humidity and temperature of the breathing gas removed for measuring purposes.

6 Claims, 1 Drawing Figure

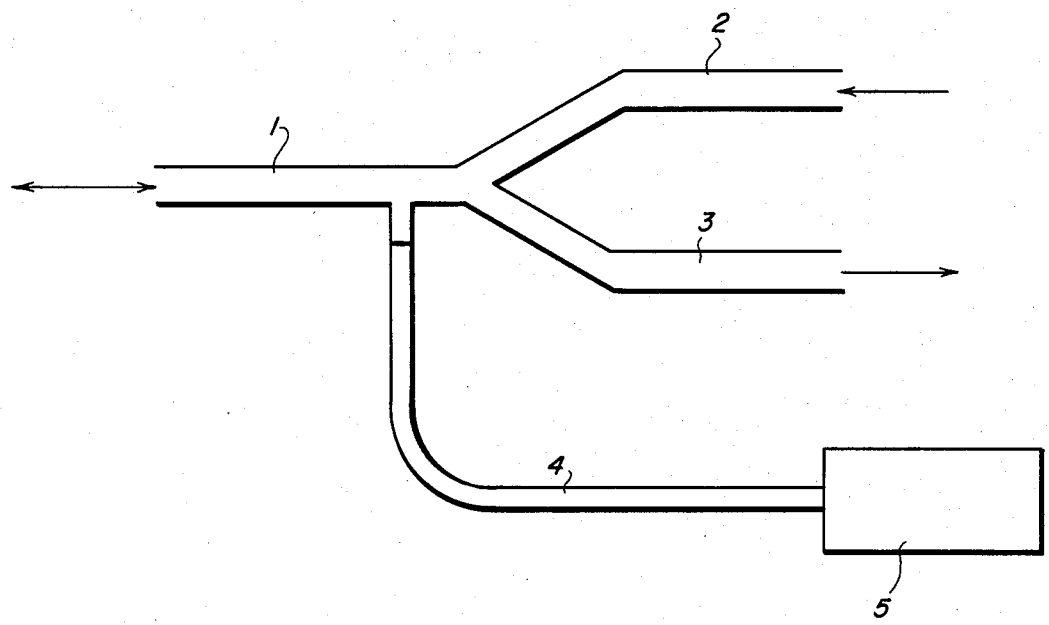

METHOD AND APPARATUS FOR MEASURING THE CONCENTRATION OF A GIVEN COMPONENT IN A GAS INHALED AND/OR EXHALED BY A PATIENT

BACKGROUND OF THE INVENTION

The present invention relates to a method for measuring the concentration of a given component in a gas inhaled and/or exhaled by a patient, and to apparatus with which the method can be carried out.

The possibility of determining the composition of the breathing gas in the pulmonary alveoli of a patient is of great interest to the medical field. In intensive care and under anaesthetic, the prime reason for this is because patients could then be more readily supervised and their treatment more favorably adapted. In the field of physiological research, the composition of the breathing gas is determined in order, among other things, to provide improved diagnostic methods. Those components whose concentration in the gas is of primary interest are $CO_2$, $O_2$ and gaseous anaesthetics such as $N_2O$, halothane, etc. It must be possible to measure the concentration of these components continuously, and preferably with a short response time so as also to enable rapid variations in concentration of the gaseous components of interest to be determined effectively. For example, the amount of oxygen ($O_2$) consumed by a patient can be determined by measuring the $O_2$-content of the breathing gas taken in and expelled by the patient during the inspiration and expiration periods.

The only location where it is practically possible to determine the concentration of a given component of the gaseous mixture inhaled and exhaled by the patient is immediately in front of the mouth of the patient, in the gas line which is connected to the patient's air passages and through which both the inhaled and exhaled gas passes. It should be possible to carry out such a determination with the aid of a transducer disposed in the path of the gas flowing through the aforesaid gas line, at least in the case of certain components of the gas. However, this would place high demands on the measuring transducer, which must be very small and light in weight, besides being capable of withstanding all manner of handling treatment, including cleaning and sterilization. For these reasons, it is preferred to withdraw part of the breathing gas flowing through the line connected to the air passages of the patient, at a location immediately in front of the patient's mouth, and to pass this part flow to a suitable instrument for determining the concentration of the gas component or components of interest in the gaseous mixture. When using this measuring method, however, it is necessary that only a relatively small gas flow is withdrawn and supplied to the measuring instrument. Moreover, the total volume of withdrawn gas between the tapping location and to the measuring instrument must be small, and the time used by the withdrawn gas to reach the measuring instrument must also be short, in order to obtain a rapid measuring response with no risk of different parts of the withdrawn breathing gas mixing together before the gas flow reaches the measuring instrument. Otherwise, it will not be possible to measure rapid variations in the concentration of the gas component of interest in a satisfactory manner.

One difficult problem encountered when carrying out this procedure, is that the relative humidity of the gaseous mixture withdrawn for measurement can vary from nearly 0% to about 97%, while the temperature of the mixture may vary from room temperature to about 35° C. This means that the amount of water carried by the withdrawn gaseous mixture can vary greatly, which leads to all manner of difficulties.

With the total pressure of the gaseous mixture constant, variations in the relative humidity of the gaseous mixture withdrawn for measurement will naturally lead to corresponding variations in the partial pressures of all the other gas components of the mixture. On the other hand, the temperature and the relative humidity in the patient's lungs are both constant. Consequently, the measuring values obtained with respect to the gas component or components of interest must be converted to the conditions prevailing in the lungs of the patient. This requires complicated measurements to be made of the momentary humidity and temperature of the gas mixture supplied to the measuring instrument. It will be understood that this problem exists even though the measuring instrument used is, in itself, insensitive to water vapor, since the variations in the content of water vapor contained in the gas mixture give rise to variations in the contents of all other gas components in the gas mixture, when said mixture is at constant pressure.

The difficulties will, of course, be still greater when the measuring instrument used is sensitive to water vapor, so that measurement of the gas component or gas components of interest is disturbed by the presence of water vapor in the gas mixture. This is the case, for example, with gas concentration detectors incorporating a crystal oscillator whose crystal has a coating which absorbs the gas component or components to be measured, for example a gaseous anaesthetic, and which is also able to absorb water vapor, such that the water-vapor content of the gas mixture will influence the measuring result. Another example is those instruments based on IR-absorption and used for determining, inter alia, $CO_2$-contents. These instruments at present use a wavelength of about 4.3 $\mu$m, which means that the measuring process will be disturbed by the presence of $N_2O$ and $O_2$ in the gas mixture. For this reason, it would be to better advantage if there could be used a wavelength of about 2.6 $\mu$m, for which wavelength many good IR-radiation detectors are available. At this wavelength, however, the measuring process is greatly disturbed by variations in the amount of water vapor contained in the gas mixture.

Another difficulty which can occur when the relative humidity and the temperature of the withdrawn gas mixture to be measured are high, is that the water vapor contained in the gas mixture condenses in the pipe or similar line leading to the measuring instrument, and/or in the measuring instrument itself, resulting in clogging of the pipe and damages to the instrument, respectively.

These difficulties could be minimized by drying the gas mixture withdrawn for measurement prior to supplying it to the measuring instrument, either by causing the water vapor in the gas mixture to condense and collecting the condensation in a water trap, or by passing the gas mixture through a suitable drying agent capable of absorbing the water vapor in the gas mixture, so that in both cases a substantially dry gas mixture is supplied to the measuring instrument. Both of these solutions to the problem, however, have been found in practice to be either unusable or highly unsuitable. For example, the water trap or the drying device must be regularly superintended, a task which is considered troublesome by those using the measuring equipment. A more serious disadvantage with these solutions, however, is that the presence of a water trap or a drying device results in an increase in the volume of gas between the tapping location and the measuring instrument and also in the time taken for the gas mixture to pass from the tapping location to said measuring instrument, which, as mentioned in the aforegoing, results in a lengthening of the measurement response time, so that rapid variations in the concentration of the gas component of interest cannot readily be detected. This problem can only be counteracted by increasing the flow of gas withdrawn for measurement. On the other hand, such an increase in the withdrawn gas flow is not desirable, since only a small part of the total volume of gas inhaled and/or exhaled by the patient should be withdrawn for measuring purposes; and said total volume may, in itself, be small, such as when treating children for example.

SUMMARY OF THE INVENTION

Consequently, an object of the present invention is to provide an improved method for measuring the concentration of one or more given components in a gas mixture inhaled and/or exhaled by a patient, in which a small part of the flow of breathing gas through a breathing-gas line connected to the air passages of the patient is continuously withdrawn and supplied to a measuring instrument sensitive to the gas component or components of interest, said method significantly reducing all of the aforediscussed problems.

This object is realised in accordance with the invention by a method of the aforementioned kind in which the temperature and the relative humidity of the gas withdrawn for measurement are adjusted to substantially coincide with the temperature and relative humidity of the ambient air prior to the gas being supplied to the measuring instrument.

The invention is based on the realisation that it is not at all necessary to totally free the gas withdrawn for measurement from water vapor prior to passing the gas to the measuring instrument, but that a fully satisfactory result can be achieved by bringing the humidity and temperature of the gas withdrawn for measurement substantially into agreement with the temperature and relative humidity of the ambient air. As will be understood, the measuring instrument can be readily calibrated prior to the measuring operation with respect to the humidity and temperature of the ambient air, which for the duration of the measuring operation will not change to any degree likely to greatly influence the accuracy of the measurements taken.

The relative humidity and temperature of the gas mixture withdrawn for measurement can be readily brought to the humidity and temperature of the ambient air by passing the withdrawn gas mixture to the measuring instrument through a line which over at least a part of its length consists of a material exhibiting high, selective and reversible water-absorption properties and the outer surfaces of which are in free contact with the ambient air. This section of the line may, to advantage, comprise a thin tube of a material comprising a fluorosulfonyl polymer or a copolymer of fluorosulfonyl and other monomers, such as tetrafluorethylene. If a gas is passed through a line, for example a thin tube, of a such material, whose outer surfaces are in free contact with the ambient air, the relative humidity of the gas flowing through the line is rapidly and effectively equalized into agreement with the humidity of the ambient air, owing to the fact that water vapor diffuses through the wall of the line towards the side of said wall on which the lower relative humidity lies. As will be understood, the temperature of the gas flowing through the line is, at the same time, brought into agreement with the temperature of the ambient air by thermal exchange therewith. All that need be ensured is that the outer surfaces of the line are in free contact with the ambient air and that the ambient air is able to flow across said surfaces.

BRIEF DESCRIPTION OF DRAWING

The drawing shows a schematic representation of a preferred embodiment of the apparatus of this invention.

DETAILED DESCRIPTION OF THE PREFERRED EMBODIMENTS

The drawing shows a breathing gas line 1, one end of which is adapted to be connected to the air passages of a patient. The opposite end of the breathing line 1 is connected to an inhalation line 2 and an exhalation line 3, which are connected to a respirator or lung ventilator (not shown). For measuring the concentration of given components of the gaseous mixture inhaled and exhaled by the patient, a small part of the gas flow through the breathing gas line 1 is withdrawn from the line 1 through a thin tube 4 and passed to a suitable measuring instrument 5 of any conventional type, which is capable of measuring the concentration of said given gas components in the gas received through the tube 4. According to the invention, the tube 4 consists, at least over part of its length, of a material having high selective and reversible water-absorption properties. Further, at least that part of the tube 4 has its outer surfaces in free contact with the ambient air. In this way, what is achieved is that the relative humidity and the temperature of the gas withdrawn from the breathing gas line 1 through the tube 4 and passed to the measuring instrument 5 will be brought into substantial agreement with the relative humidity and the temperature of the ambient air, before the gas reaches the measuring instrument 5. The material in the tube 4 may preferably be a fluorosulphonylpolymer.

When applying the method according to the invention, only a very small flow of gas need be withdrawn and supplied to the measuring instrument, and since the length of tube needed is relatively short the time taken for the gas to pass from the tapping location to said measuring instrument is short and the risk of internal mixing of the withdrawn gas is minimal, thereby enabling even rapid changes in the concentration of the gas component of interest to be measured. When applying the method according to the invention, the amount of gas withdrawn for measurement depends upon the requirements of the measuring instrument used.

As will be understood, the requisite length of the tube of the water-vapor reversibly absorbing material will depend upon the size of the gas flow and the diameter of the tube, and on the magnitude of the difference in the relative humidities to be equalized. These values, however, can be readily established by tests.

In order to determine the efficiency of the method according to the invention, a number of tests were carried out in which air of a given relative humidity was passed into one end of a commercially available tube made of a fluorosulfonyl copolymer, the outer surfaces of which tube were in free contact with the ambient air.

and the relative humidity of the air exiting from the other end of the tube was measured. These tests were carried out with tubes of mutually different lengths and with two different rates of flow through the tube, namely 100 ml/min and 400 ml/min respectively. The tubes had an outer diameter of about 1.25 mm and an inner diameter of about 1.0 mm in all tests.

Test 1

In this test the air introduced into one end of the tube had a relative humidity of 96% and a temperature of 23° C., while the air surrounding the tube had a relative humidity of 25% and a temperature of 23° C. Test 2

In this test, the air introduced to one end of the tube had a relative humidity of 2% and a temperature of 23° C., while the air surrounding the tube had a relative humidity of 24% and a temperature of 23° C.

The results of these tests are shown in the Table below, which sets forth the relative humidity of the air exiting from the other end of respective tubes of mutually different lengths.

TABLE

| Tube length cm | Test 1 | | Test 2 | |
|---|---|---|---|---|
| | Flow rate 400 ml/min | Flow rate 100 ml/min | Flow rate 400 ml/min | Flow rate 100 ml/min |
| 100 | 24 | 24 | 23 | 23 |
| 90 | 25 | 24 | 23 | 23 |
| 80 | 26 | 24 | 23 | 23 |
| 70 | 28 | 24 | 23 | 23 |
| 60 | 33 | 24 | 23 | 23 |
| 50 | 36 | 24 | 23 | 23 |
| 40 | 39 | 24 | 21 | 23 |
| 30 | 48 | 24 | 18 | 23 |
| 20 | 61 | 32 | 12 | 23 |
| 10 | 79 | 62 | 6 | 20 |

It will be clear from these results that when practicing the method according to the invention using a relatively short tube, the relative humidity of the gas flowing through the tube can be brought into agreement with the humidity of the surrounding air irrespective of whether the original relative humidity of the gas flowing through said tube was much higher or much lower than that of the ambient air.

It will also be understood that the invention can be applied irrespective of the form taken by the measuring instrument used to measure the concentration of the gas component or components of interest.

We claim:

1. A method for measuring the concentration of at least one given component in a breathing gas passing through a breathing-gas line connected to the air passages of a patient, comprising the steps of withdrawing continuously a small part of the gas flow passing through said breathing-gas line, bringing the relative humidity and temperature of said withdrawn gas into substantial agreement with the relative humidity and temperature of the ambient air, and subsequently supplying said withdrawn gas to a measuring instrument sensitive to the concentration of said component.

2. A method as claimed in claim 1, wherein the relative humidity and temperature of said withdrawn gas and the ambient air are brought into substantial agreement by passive diffusion of water vapor and thermal exchange between said ambient air and said withdrawn gas.

3. Apparatus for measuring the concentration of at least one given component in a breathing gas passing through a breathing-gas line connected to the air passages of a patient, comprising a measuring instrument sensitive to the concentration of said component in a gas mixture supplied to the instrument, means for continuously withdrawing a small part of the gas flow in said breathing-gas line, and a line connecting said gas-withdrawing means with said measuring instrument, said connecting line consisting, at least over part of its length, of a material having high, selective and reversible water-absorption properties, and having at least over said part of its length its outer surfaces in free contact with the ambient air.

4. Apparatus as claimed in claim 3, wherein said connecting line comprises a tube made of a fluorosulfonyl polymer.

5. A method for measuring the concentration of at least one given component in a breathing gas passing through a breathing-gas line connected to the air passages of a patient, comprising the steps of withdrawing continuously a small part of the gas flow passing through said breathing-gas line, bringing the relative humidity and temperature of said withdrawn gas into substantial agreement with the relative humidity and temperature of the ambient air by passing said withdrawn gas through a line which, over at least part of its length, consists of a material having high selective and reversible water-absorption properties, and the outer surfaces of which are in free contact with the ambient air and subsequently supplying said withdrawn gas to a measuring instrument sensitive to the concentration of said component.

6. A method as claimed in claim 5, wherein said line comprises a tube made of a fluorosulfonyl polymer.

* * * * *